US006566326B1

(12) United States Patent
Soltero et al.

(10) Patent No.: US 6,566,326 B1
(45) Date of Patent: May 20, 2003

(54) CHEMICALLY MODIFIED HEMOGLOBIN FOR BURN SHOCK RESUSCITATION

(75) Inventors: Raluan G. Soltero, La Jolla, CA (US); Kenneth E. Burhop, Mundelein, IL (US); John F. Hansbrough, Rancho Santa Fe, CA (US)

(73) Assignee: The Regents of the University of California, Oakland, CA (US)

( * ) Notice: Subject to any disclaimer, the term of this patent is extended or adjusted under 35 U.S.C. 154(b) by 1329 days.

(21) Appl. No.: 08/615,058

(22) Filed: Mar. 13, 1996

(51) Int. Cl.$^7$ ............................................... A61K 38/16
(52) U.S. Cl. ............................................. 514/6; 530/385
(58) Field of Search ..................... 514/6, 833; 530/385

(56) References Cited

U.S. PATENT DOCUMENTS

| | | | | |
|---|---|---|---|---|
| 4,001,401 A | | 1/1977 | Bonsen et al. .................. | 514/6 |
| 4,529,719 A | * | 7/1985 | Tye ................................. | 514/6 |
| 4,598,064 A | * | 7/1986 | Walder .......................... | 514/6 |
| 4,861,867 A | | 8/1989 | Estep ........................... | 530/385 |
| 5,039,520 A | * | 8/1991 | Hunter ......................... | 424/83 |
| 5,084,558 A | | 1/1992 | Rausch et al. ............... | 530/385 |
| 5,334,706 A | * | 8/1994 | Przybelski ................... | 530/385 |
| 5,428,007 A | * | 6/1995 | Fischer et al. ................ | 514/6 |
| 5,443,848 A | * | 8/1995 | Kramer et al. .............. | 424/643 |

OTHER PUBLICATIONS

Nguyen et al. Current treatment of severly burned patients. Annals of Surgery. vol. 223, No. 1, pp. 14–25, 1996.*
Gulati et al. Cardiovascular effects of unmodified stroma-free (SFHb) abd diaspirin crosslinked (DCLHb) hemoglobin. Canadian Journal of Physiological Pharmacology. vol. 72 (suppl. 1) Abstract P1.12.8, 1994.*
Sharma et al. Regional circulatory and systemic hemodynamic effects of diaspirin cross–linked hemoglobin in the rat. Art. Cells., Blood Subs., and Immob. Biotech. vol. 22, No. 3, pp. 593–602, 1994.*
Bamberger et al., "Nitric Oxide Mediates the Depression of Lymphoproliferative Responses Following Burn Injury in Rats," *Biomed. & Pharmacother.* 46:495–500 (1992).
Carter et al., "Nitric Oxide Production is Intensely and Persistently Increased in Tissue by Thermal Injury," *Biochem. J.* 304:201–204 (1994).

Cohen and Farrell, "Diaspirin Cross–Linked Hemoglobin Resuscitation of Hemorrhage: Comparison of a Blood Substitute with Hypertonic Saline and Isotonic Saline," *Trauma J.* 39:210–217 (1995).
Frankel et al., "Diaspirin Cross–Linked Hemoglobin is Effecacious in Gut Resuscitation as Measured by a GI Tract Optode," *Trauma J.* 40:231–241 (1996).
J.A. Jones, "Red Blood Cell Substitutes: Current Status," *Br. J. Anaesth.* 74:697–703 (1995).
Leppäniemi et al., "Early Resuscitation with Low–Volume PolyDCLHb is Effective in the Treatment of Shock Induced by Penetrating Vascular Injury," *Trauma J.* 40:242–248 (1996).
Morehouse et al., "Resuscitation of the Thermally Injured Patient," *Critical Care Clinics* 8:355–365 (1992).
Mourelatos et al., "The Effects of Diaspirin Cross–Linked Hemoglobin in Sepsis," *Shock* 5:141–148 (1996).
Preiser et al., "Nitric Oxide Production is Increased in Patients after Burn Injury," *Trauma J.* 40:368–371 (1996).
Schultz et al., "A Role for Endothelin and Nitric Oxide in the Pressor Response to Diaspirin Cross–Linked Hemoglobin," *J. Lab Clin. Med.* 122:301–308 (1993).
Schultz et al., "The Efficacy of Diaspirin Cross linked Hemoglobin Solution Resuscitation in a Model of Uncontrolled Hemorrhage," *Trauma J.* 37:408–412 (1994).
Schultz et al., "Use of Base Deficit to Compare Resuscitation with Lactated Ringer's Solution, Haemaccel, Whole Blood, and Diaspirin Cross–Linked Hemoglobin Following Hemorrhage in Rats," *Trauma J.* 35:619–626 (1993).
Zapata–Sirvent et al., "Effects of Fluid Resuscitation, Burn Eschar Excision, and Blockade of Afferent Pain Response on Bacterial Translocation and Acid–Base Balance After Murine Burn Injury," *J. Burn Care & Rehab.* 14:495–502 (1993).

* cited by examiner

Primary Examiner—Michael Pak
(74) *Attorney, Agent, or Firm*—Brown Martin Haller & McClain LLP

(57) ABSTRACT

Hemoglobin chemically modified to reduce oxygen affinity and prevent dissociation are administered parenterally during resuscitation to patients suffering from burn shock. Such treatment, reduces base deficit, increases cardiac output and mean arterial blood pressure, and improves survival.

9 Claims, 3 Drawing Sheets

CHEMICALLY MODIFIED HEMOGLOBIN FOR BURN SHOCK RESUSCITATION

FIELD OF THE INVENTION

The present invention relates to the field of trauma intervention, and in particular, the treatment of severe burns with parenteral therapy involving administration of chemically modified hemoglobin.

BACKGROUND OF THE INVENTION

The occurrence of severe burn injury sets in motion a complex series of biochemical and physiological events that critically affect the course of recovery and even the survival of the patient. In the early hypodynamic stage of burn shock, there is a marked suppression of mean arterial blood pressure (MAP), cardiac output (CO), systemic vascular resistance (SVR), oxygen delivery (DO2), and an increase in base deficit. Associated with these changes is a profound increase in capillary permeability resulting in extravasation of large amounts of plasma fluids. Most of these fluids are retained in the extravascular tissue matrix as edema.

Many of these effects are mediated by vasoactive hormones and other substances. Levels of IL-1, IL-6, vasopressin and nitric oxide are elevated, and contribute to the systemic effects. At the local inflammatory level, products of arachidonic acid metabolism such as leukotrienes and prostaglandins increase microvascular permeability. Thromboxane A2, and related metabolites, are produced locally in the burn wound and cause injury by increasing tissue ischemia. Other vasoactive mediators, such as histamine, bradykinin, and oxygen radicals generated post-burn contribute to edema either directly by affecting vascular permeability, or indirectly by causing an increase in microvascular hydrostatic pressure.

A marked decrease in the delivery of oxygen to the burn wound is a consequence of reduced CO, lower MAP, reduced cardiac contractility, and the edema which interferes with tissue perfusion because of occlusion of capillaries. Resolution of the hypodynamic state with progression to the hyperdynamic stage is imperative. Failure to achieve this transition is correlated with increased mortality. Reversal of base deficit, and stabilization of cardiac parameters during the first 36 hours post-trauma, may be correlated with enhanced survival.

By the 1970's, the importance of restoring circulating fluid volume by administration of resuscitative fluids was well recognized. Several regimens were developed to calculate the desired resuscitative fluid volume. The use of colloid and crystalloid solutions is described in detail in Demling, et al., Burn Trauma, Thieme Medical Publishers: New York (1989). The Parkland formula requires administration of 4 mL Ringer's Lactate/kg of body weight divided by the percent total burn surface area (TBSA) during the first 24 hours post-burn. In the Brooke formula, 2 mL Ringer's Lactate/kg of body weight divided by TBSA is supplemented with 2000 mL of 5% dextrose during the first 24 hours post-burn trauma. A third formula utilized by the Shriners Burn Institute is composed of Lactated Ringer's solution containing 1.25% salt-poor human albumin, administered in a quantity of 2000–500 mL in a 24 hour period.

The foregoing fluid replacement treatments, while generally beneficial in restoring circulating volume, may actually impede tissue perfusion. The continued extravasation of the large amount of infused fluid exacerbates edema and decreases oxygen delivery systemically and at the burn site. The various resuscitative formulae involving colloids improve oncotic pressure, but do not regularly result in an improvement in clinical outcome. In some instances, life threatening complications may occur which are directly attributable to treatment, as in the occurrence of pulmonary edema in the administration of oncotic solutions.

SUMMARY OF THE INVENTION

The present invention provides a method of treating burn shock, by administration of hemoglobin chemically modified to decrease its affinity for oxygen. Chemically modified hemoglobin having a $P_{50}$ value of about 20–55, preferably 25–35, is administered in for example, a resuscitative fluid to provide a total cumulative quantity of 100 to 2000 mg/kg of body weight. The resuscitative solution can be, for example, Lactated Ringer's solution.

In one embodiment, the hemoglobin chemically modified to decrease its affinity for oxygen is administered in a resuscitation fluid volume delivered in a cumulative dose of 100 to 2000 mg/kg of body weight during the course of a fluid resusucitation regimen. The resuscitation regimen can be selected from any one of the established protocols such as the Parkland formula, Evans formula, Brooke formula, or accepted variants thereof. Administration time is generally about 24 hours post-burn, but the time may be shortened or expanded depending on the fluid condition of the patient.

In some of the treatment protocols the rate of administration may vary over the course of the first 24 hours post-burn. For example, in the Parkland formula, half of the resuscitative fluid volume is administered during the first 8 hour period, and the remaining half of the fluid volume is administered during the remainder of 24 hours post-burn. A resuscitative solution containing hemoglobin may be administered according to this or other established formula.

DETAILED DESCRIPTION OF THE INVENTION

Figure 1:
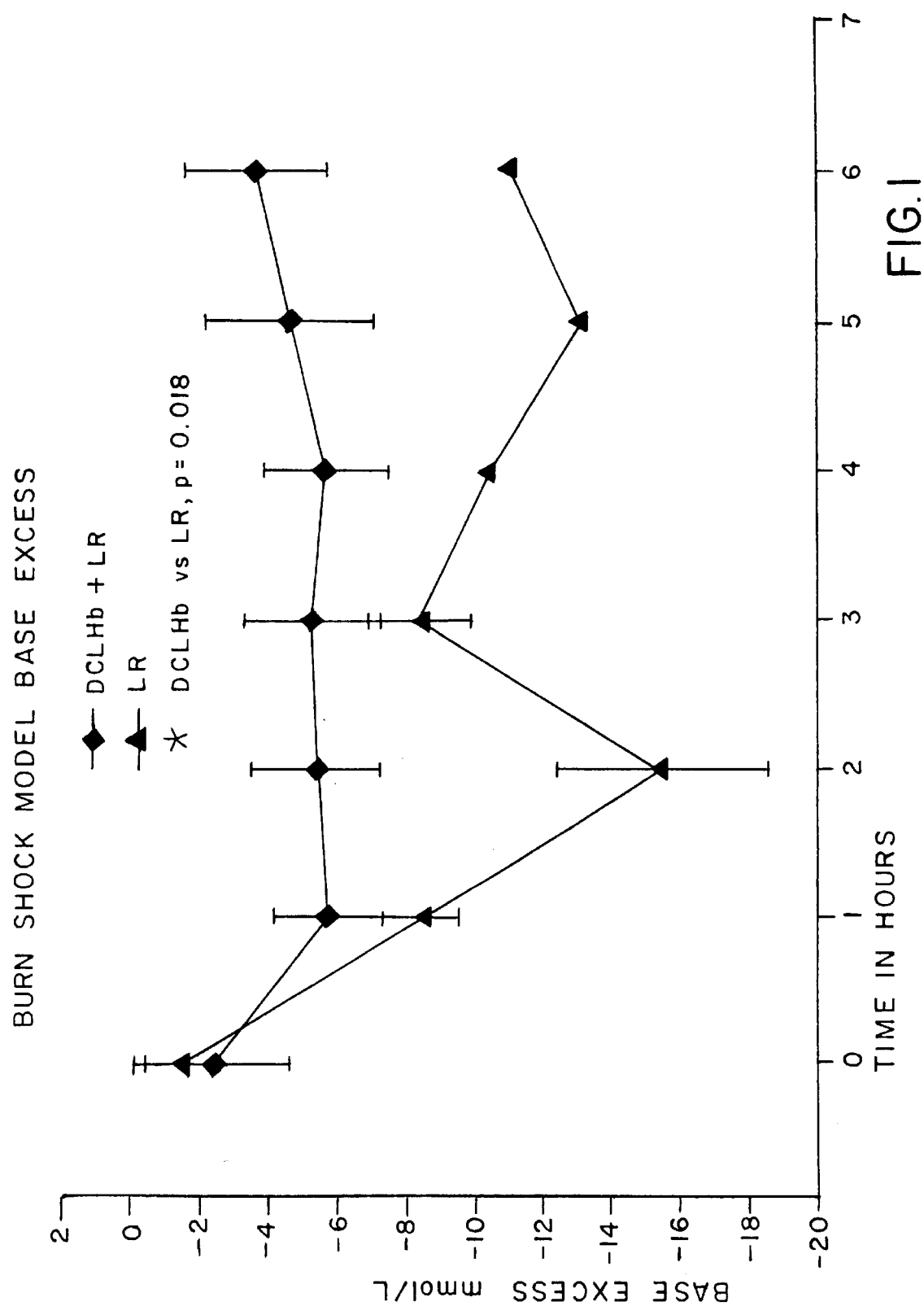
FIG. 1 is a rectilinear plot of the DCLHb and control group values for base excess post-burn.

It is an object of the present invention to provide a treatment for burn shock which accelerates reduction of base deficit, increases cardiac output and mean arterial blood pressure, and promotes conversion of the hypodynamic state post-burn to a hyperdynamic condition within 24 to 36 hours. It is a further object to increase perfusion locally at the site of the burn lesion, and also to other tissues including the gut and organ systems to prevent or reduce tissue ischemia and prevent other long-term consequence such as bacterial translocation and pulmonary edema.

In the treatment of burn shock, administration of large amounts of parenteral fluid during the first 24 hours post-burn has become standard. In general, these treatments take into account the size of the burn lesion. The larger the wound, the more fluid is administered. At increasing %TBSAs, more fluid is given according to the formula being followed. In the Parkland formula, the amount of total fluid to be given in the first 24 hours is calculated as follows: 4×%TBSA×weight in kilograms. In the Evans formula a colloid solution is administered at the rate of 1 mL/kg/

%TBSA simultaneously with a crystalloid solution (preferably Lactated Ringer's solution) at the rate of 1 mL/kg/%TBSA and 2000 of physiologic saline. The Brooke formula differs from the Evans formula, only in that the colloid solution is reduced to 0.5 mL, and the crystalloid solution is increased to 1.5 mL. For a detailed description of these regimens and the solution constituents, see Nguyen, et al., Annals of Surgery, 223:14 (1996), hereby incorporated by reference.

In some of these regimens, the delivery of solution is front loaded, so that the patient receives solution at a higher flow rate during the first few hours. In the practice of the present invention, the concentration of hemoglobin does not need to be changed for differing flow rates. The pharmacologic and physiological effects of hemoglobin are manifest over the stated ranges, so that varying the amounts infused in unit time as a function of intravenous flow rate is of no adverse consequence. In fact, infusion of larger amounts of hemoglobin in unit time at the beginning of treatment may have the benefit of enhancing perfusion in the early critical hours after trauma, when tissue at risk may yet be salvaged.

The various treatment regimens for parenteral fluid replacement in severe burns have been developed from patient retrospectives. For a description of the development of these approaches, see Martyn, J. A. J., Acute Management of the Burned Patient, W. B. Saunders: Philadelphia, Pa. (1990), incorporated herein by reference. Since the reversal of base excess and improvement in cardiac parameters occur relatively early in treatment, conversion to the hyperdynamic state may ensue earlier also. This means that as more data are gathered from animal and patient populations, the standard regimens may be modified to administer less resuscitative liquid volume. The benefit will be to reduce the edema, which is one of the complications in the management of severe burns.

The hemoglobin used in the present invention can have a methemaglobin content of less than 15 percent, be free of infectious disease agents, and have a high level of purity (less than 0.3% contaminating blood-derived proteins and less than 0.1 U of endotoxin). The hemoglobin solution may be added by any conventional method to standard colloid or crystalloid solutions to achieve the proper concentration. The hemoglobin can be maintained in a frozen state. Alternatively, colloid or crystalloid ingredients can be added to dilute hemoglobin solutions, and then can be stored at refrigerated temperatures. This latter method can be appropriately used at trauma or burn centers where demand for parenteral solutions may be essentially continuous.

The hemoglobin utilized in the present invention may be of any type which is stroma-free and modified chemically to increase the oxygen binding affinity to the range of $P_{50}$, values between about 20 and 55 mm Hg. The $P_{50}$ value is defined as the $pO_2$ needed to saturate with oxygen 50% of the functional heme molecules contained in hemoglobin. The modified hemoglobin may be a conjugated hemoglobin, cross-linked hemoglobin, or polymerized hemoglobin.

Several examples of hemoglobin modification technology have been described in the scientific literature which may be used to advantage in the practice of the present invention. For example, see the review contained in Winslow, R. M., Hemoglobin-based Red Cell Substitutes, The John Hopkins U. Press (1992), incorporated herein by reference. More specifically, the methods of making chemically modified hemoglobin are set forth hereinafter. Hemoglobin modification can be by conjugation, cross-linking or polymerization A conjugated hemoglobin is one to which a non-protein macromolecule is bound covalently to hemoglobin. One example is a hemoglobin chemical modified by polyalkylene glycol, which is described together with a process for its preparation in WO 9107190. An example of a hemoglobin conjugated to poly(alkylene oxide) and a process for its preparation are provided in U.S. Pat. Nos. 4,301,144, 4,412,989 and 4,670,417, and in Japanese Patent Nos. J59,104,323 and J61,053,223. Hemoglobin may be conjugated to inulin in a process disclosed in U.S. Pat. No. 4,377,512. The patents WO 9107190, U.S. Pat. Nos. 4,301, 144, 4,670,412, 4,377,512 and Japanese Patent Nos. J59, 104,323 and J61,053,223 are hereby incorporated by reference.

A cross-linked hemoglobin contains an intramolecular chemical link. Examples of cross-linked hemoglobins and methods for their preparation are described in U.S. Pat. Nos. 4,001,401 and 4,053,590, which disclose intramolecular cross-linking between an alpha and beta subunit of a hemoglobin tetramer utilizing compounds such as halogenated cycloalkanes, diepoxides, and diazobenzidines. In the present method, a modified hemoglobin is cross-linked with bis(3,5-dibromosalicyl)fumarate to create a fumarate cross-link between the two alpha subunits. This cross-linked hemoglobin is more fully described, together with methods for its preparation, in U.S. Pat. Nos. 4,598,064, 4,600,531, RE 34,271, omitting the chromatography step. It can be manufactured under the conditions disclosed in U.S. Pat. No. 5,128,452 (Hai) to prevent cross-linking between beta and chains. U.S. Pat. Nos. 4,598,064, 4,600,531, RE 34,271 and 5,128,452 are hereby incorporated by reference. WO 9013309 (Staat Der Nederlanden De Minister Van Defeuric) discloses a method for cross-linking hemoglobin through a α–α linkage. The preferred diaspirin cross-linked hemoglobin will hereafter be referred to as "DCLHb".

A polymerized hemoglobin is one in which intermolecular cross-linking of hemoglobin tetramers has been used to increase the molecular weight of the modified hemoglobin. For example, U.S. Pat. No. 4,777,244 discloses a method for cross-linking and polymerizing with aliphatic dialdehydes. The foregoing patents are hereby incorporated by reference.

A hemoglobin that has been modified by a combination of methods is exemplified by the following. Hemoglobins modified by pyridoxal-5'-phosphate to adjust the oxygen affinity and by polyethylene glycol conjugation and processes for its preparation are described in Japanese Patent Nos. J59,089,629, J59,103,322 and J59,104,323 (Ajinomoto). U.S. Pat. No. 5,248,766 discloses a cross-linking polymerizing strategy and a process for covalently interconnecting tetrameric units with oxiranes to form polyhemoglobins with molecular weights in excess of 120,000 daltons. The foregoing patents disclosing polymerized hemoglobins, U.S. Pat. Nos. 5,194,590, 5,248,766, Japanese Patent Nos. J59,103,322, J59,089,629 and J59,104,323, are hereby incorporated by reference.

Hemoglobin may be modified by site-directed mutagenesis and expressed in micro-organisms or transgenic animals. Recombinant mutant and artificial hemoglobin and its production in cell cultures or fluids is described in U.S. Patent 5,028,588 (Somatogen). Di-alpha and di-beta globin-like polypeptide(s) used for production of hemoglobin in bacteria and yeast are described in WO 9013645 (Somatogen). A non-natural multimeric hemoglobin-like protein is described in WO 9309143 (Somatogen). In general any method of cross-linking, polymerizing, or genetically modifying, or combination thereof which yields a base tetramer having a $P_{50}$ in the operative range of 20 to 45 mm Hg will have efficacy in the present method. Conditions may be adjusted for each such cross-linked tetramer or polymer derived therefrom without undue experimentation.

Finally, a particularly preferred diaspirin cross-linked hemoglobin has recently been developed (as disclosed in co-pending U.S. patent application Ser. No. 08/532,293), in which a special heat treatment sterilization step results in precipitation of impurities, yielding a supernatant pure enough to obviate a subsequent chromatography step. This process has an advantage over its predecessors in that the complete absence of chromatography fines eliminates false positive endotoxin tests. Other advantages of the present invention will be apparent from the Example which follows.

EXAMPLE

In the present experiments, male Wister rats, weighing 200–250 grams, were anesthetized with nembutal (50 mg/mL) 100 $\mu$l per 100 g of body weight (35–45 mg/kg). The dorsum of the animal was shaved and depilated using Nair (Carter Wallace Inc., New York, N.Y.). The animals underwent internal jugular vein and femoral artery catheterization with polyethylene catheters (PE 50). A thermistor probe was placed in the right carotid artery.

After the catheters were in place, baseline values were obtained (MAP, CO, Arterial and Venous blood gases). The animals were then submerged in boiling water (100° C.) for 6 seconds to obtain a 30% scald burn. The rats were randomized into one of the following two treatment groups and immediately resuscitated (The entire resuscitation volume was given intravenously through the jugular vein):

Group I: Standard crystalloid resuscitation at the rate:
(Ringer's Lactate 4 mL/kg/% TBSA over 24 hours) (½ of that amount given in the first 8 hours) according to the Parkland formula.

Group II: LR+DCLHb resuscitation at the rate: (Ringer's Lactate 2 mL/kg/% TBSA+DCLHb 2 mL/kg/% TBSA entire amount to be given over 24 hours) (½ to be given in the first 8 hours). DCLHb was manufactured according to the general protocol described in Chatterjee, et al., J. Biol. Chem., 261:9929 (1986). Although the rate of administration was that calculated for a 24-hour infusion, the actual experiment was run for the first 6 hours. To control pain throughout the experiment animals were given buprinex (0.3 mg/kg). at 2 hours post-burn.

Hemodynamic parameters (MAP and HR) were obtained through the femoral artery using a pressure transducer connected to the Cardiomax II thermodilution Cardiac Output Computer (Columbus Instruments, Columbus, Ohio). Cardiac output (CO) was measured by thermodilution using a thermistor probe in the carotid artery (Columbus Instruments). Venous and arterial blood gases were obtained and analyzed for base excess, pH, arterial and venous oxygen content utilizing a Corning 168 Ph/Blood Gas Analyzer (Corning Glassworks, Medfield, Mass.). Systemic vascular resistance, oxygen delivery and oxygen consumption were recorded throughout the experiment.

Blood samples and hemodynamic parameters were obtained at baseline (before burn but after catheter placement) and at the following times post-burn: 1, 2, 3, 4, 5, and 6 hours. At 6 hours post-burn the animals were euthanized by an overdose of nembutal.

The results indicate that DCLHb when infused in a crystalloid solution post-burn at a rate calculated from the Parkland formula, has a positive effect on all cardiac and physiologic parameters measured. Table 1A shows a high degree of reversal of base excess compared to controls receiving only Lactated Ringer's solution (See Table 1B). The rows in the tables indicate values for individual animals. The columns represent the values for baseline (time 0) and the values obtained at each hour thereafter, up to 6 hours. Following burn, resuscitation procedures were begun immediately.

TABLE 1A

BASE EXCESS (mM/L)

| Rat # | DCLHB 0 | DCLHB 1 | DCLHB 2 | DCLHB 3 | DCLHB 4 | DCLHB 5 | DCLHB 6 |
|---|---|---|---|---|---|---|---|
| 02159602 | −1.5000 | −3.3000 | −3.9000 | −6.2000 | −3.5000 | −8.1000 | −2.4000 |
| 02239601 | −1.5000 | −7.1000 | −7.8000 | −8.3000 | −8.3000 | −2.7000 | −3.1000 |
| 02299601 | −1.1000 | −6.9000 | −5.9000 | −5.2000 | −5.9000 | −2.5000 | * |
| 02299602 | −6.4000 | −6.3000 | −6.5000 | −3.7000 | −6.5000 | −6.2000 | −2.6000 |
| 03059601 | −1.5000 | −5.3000 | −3.3000 | −3.4000 | −4.7000 | −4.2000 | −6.8000 |

*Animal alive, but unable to obtain blood sample.

TABLE 1B

BASE EXCESS (mM/L)

| Rat # | LR 0 | LR 1 | LR 2 | −LR 3 | LR 4 | LR 5 | LR 6 |
|---|---|---|---|---|---|---|---|
| 02239602 | 1.0000 | −4.9000 | −29.0000 | | | | |
| 02099602 | −5.4000 | −12.1000 | −14.3000 | | | | |
| 02099601 | −1.2000 | −5.7000 | −13.3000 | | | | |
| 02159601 | 0.1000 | −10.0000 | −18.5000 | | | | |
| 03019601 | −1.0000 | −9.4000 | −8.1000 | −7.0000 | −10.4000 | −13.0000 | −11.1000 |
| 03019602 | −1.8000 | −8.9000 | −10.0000 | −10.0000 | −10.6000 | −13.4000 | |

Figure 2:
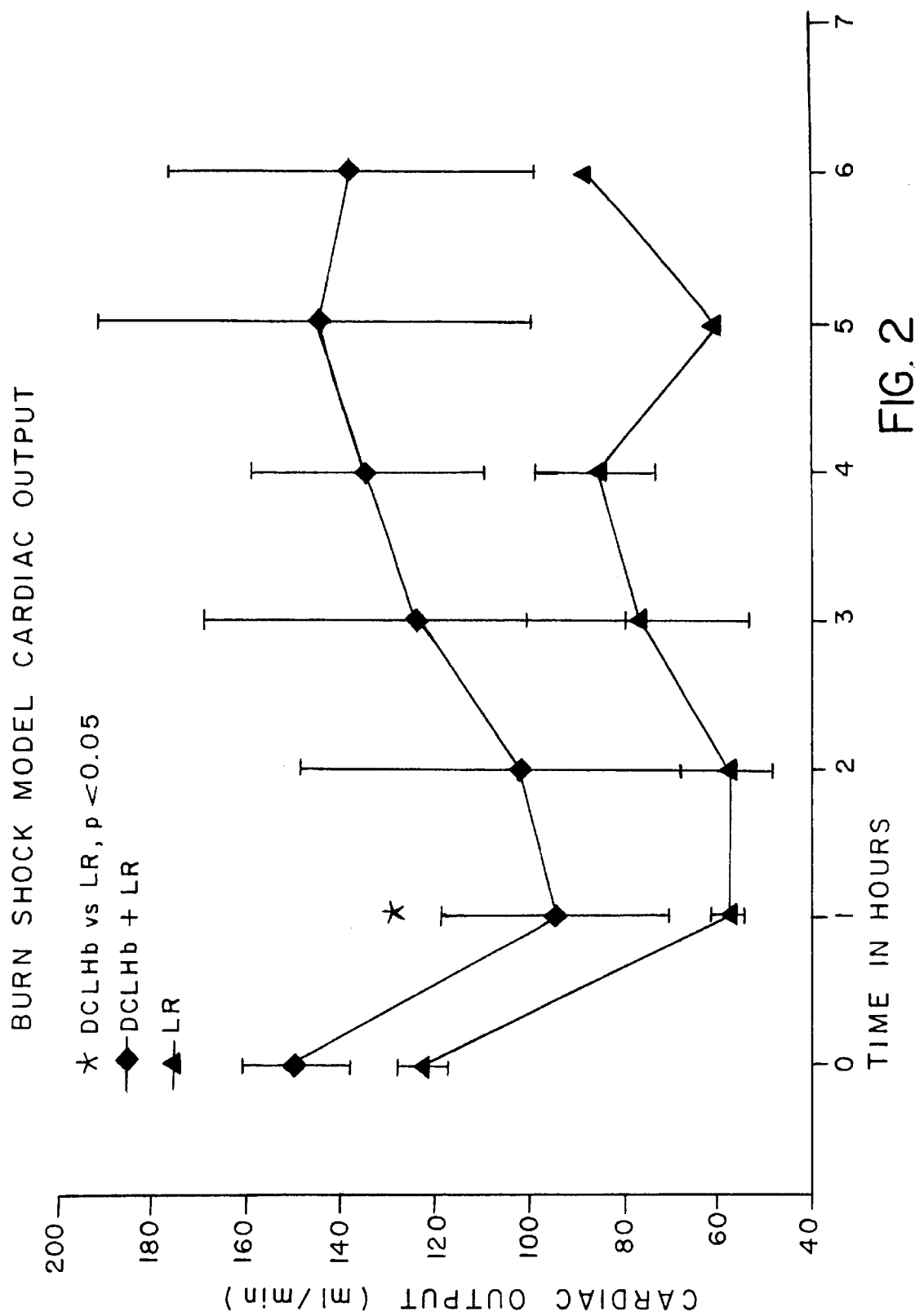
FIG. 2 is a rectilinear plot of the DCLHb and control group values for cardiac output (mL/min).
Figure 3:
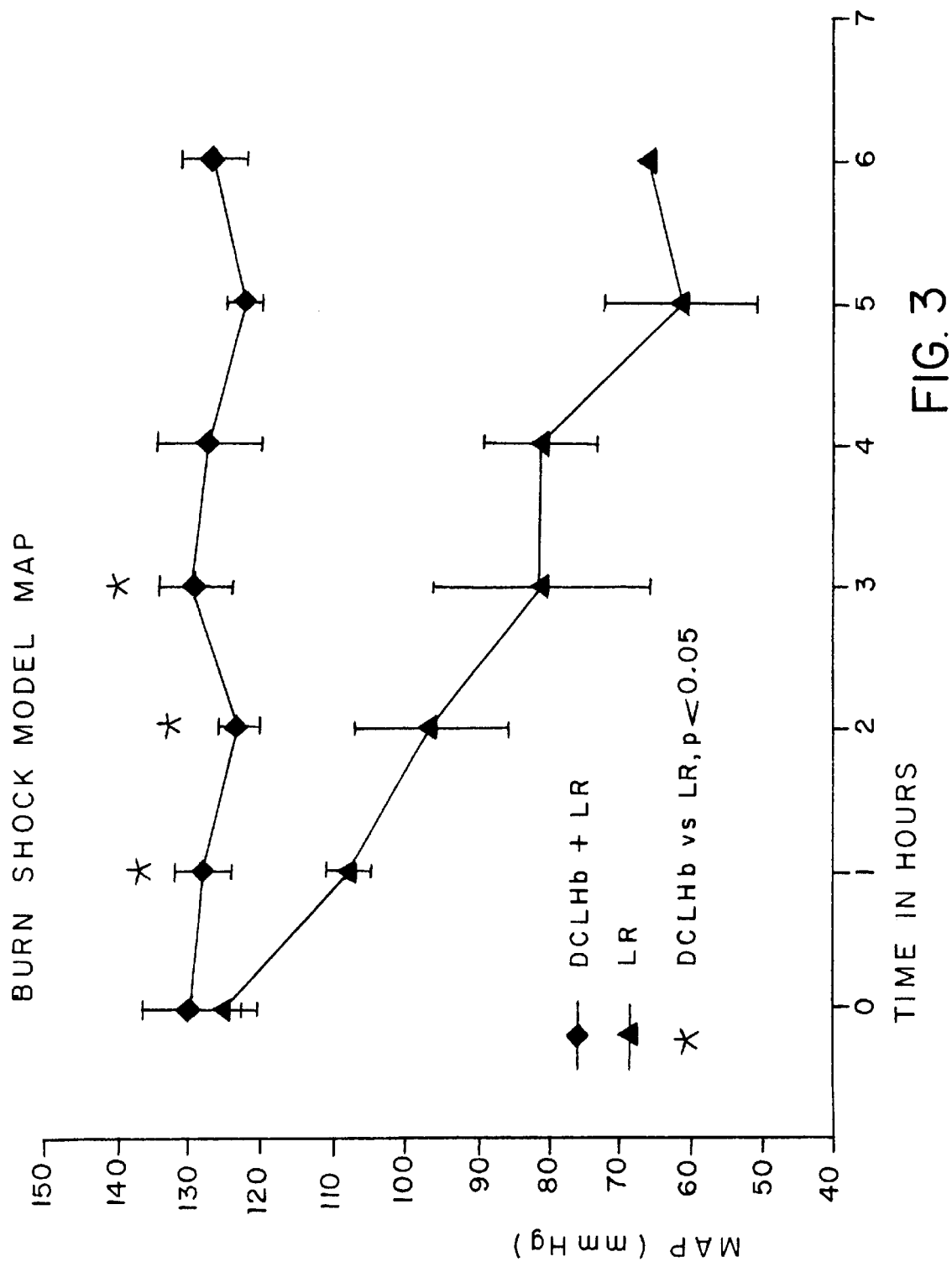
FIG. 3 is a rectilinear plot of the DCLHb and control group values for mean arterial pressure (mm Hg).

Similarly, the depression in cardiac output observed in control was uniformly reversed. (Compare Table 2A to 2B). Note also the improvement in mean arterial pressure in the DCLHb group compared to the control group (Tables 3A and 3B). The data are graphed in FIGS. 1–3 for base excess, cardiac output, and mean arterial pressure.

Most dramatic, however, was the effect of DCLHb on survival. The blank boxes in Tables 1B 2B, and 3B indicate the approximate times of spontaneous death of the animal. At the end of 6 hours, all but one control animal had expired, whereas none of the DCLHb-treated animals had died.

TABLE 2A

CARDIAC OUTPUT (mL/min)

| Rat # | DCLHB 0 | DCLHB 1 | DCLHB 2 | DCLHB 3 | DCLHB 4 | DCLHB 5 | DCLHB 6 |
|---|---|---|---|---|---|---|---|
| 02159602 | 148.0000 | 127.0000 | 180.5000 | 193.0000 | 158.5000 | 171.0000 | 180.5000 |
| 02239601 | 135.0000 | 79.5000 | 79.5000 | 112.0000 | 126.5000 | 129.0000 | 135.5000 |
| 02299601 | 144.5000 | 105.5000 | 64.0000 | 73.0000 | 108.0000 | 104.5000 | 90.5000 |
| 02299602 | 166.0000 | 64.0000 | 90.0000 | 103.5000 | 113.5000 | 107.0000 | 109.0000 |
| 03059601 | 154.0000 | 92.5000 | 94.5000 | 135.5000 | 161.0000 | 211.5000 | 170.5000 |

TABLE 2B

CARDIAC OUTPUT (mL/min)

| Rat # | LR 0 | LR 1 | LR 2 | LR 3 | LR 4 | LR 5 | LR 6 |
|---|---|---|---|---|---|---|---|
| 02239602 | 138.0000 | 67.5000 | | | | | |
| 02099602 | 104.5000 | 44.5000 | 39.0000 | | | | |
| 02099601 | 110.0000 | 53.0000 | 44.5000 | | | | |
| 02159601 | 135.5000 | 57.0000 | | | | | |
| 03019601 | 124.5000 | 59.5000 | 64.0000 | 100.0000 | 98.0000 | 60.0000 | 88.0000 |
| 03019602 | 124.0000 | 64.0000 | 82.0000 | 53.0000 | 72.5000 | 61.5000 | |

TABLE 3A

MEAN ARTERIAL PRESSURE (mm Hg)

| Rat # | DCLHB 0 | DCLHB 1 | DCLHB 2 | DCLHB 3 | DCLHB 4 | DCLHB 5 | DCLHB 6 |
|---|---|---|---|---|---|---|---|
| 02159602 | 127.0000 | 114.0000 | 113.0000 | 112.0000 | 130.0000 | 120.0000 | 120.0000 |
| 02239601 | 122.0000 | 135.0000 | 128.0000 | 138.0000 | 148.0000 | 129.0000 | 129.0000 |
| 02299601 | 156.0000 | 132.0000 | 121.0000 | 136.0000 | 123.0000 | 122.0000 | 143.0000 |
| 02299602 | 120.0000 | 127.0000 | 129.0000 | 136.0000 | 103.0000 | 114.0000 | 120.0000 |
| 03059601 | 123.0000 | 131.0000 | 123.0000 | 122.0000 | 130.0000 | 124.0000 | 120.0000 |

TABLE 3B

MEAN ARTERIAL PRESSURE (mm Hg)

| Rat # | LR 0 | LR 1 | LR 2 | LR 3 | LR 4 | LR 5 | LR 6 |
|---|---|---|---|---|---|---|---|
| 02239602 | 115.0000 | 113.0000 | 63.0000 | | | | |
| 02099602 | 132.0000 | 105.0000 | 115.0000 | 36.0000 | | | |
| 02099601 | 130.0000 | 98.0000 | 126.0000 | 97.0000 | | | |
| 02159601 | 140.0000 | 120.0000 | 71.0000 | | | | |
| 03019601 | 118.0000 | 108.0000 | 115.0000 | 102.0000 | 89.0000 | 72.0000 | 66.0000 |
| 03019602 | 116.0000 | 102.0000 | 88.0000 | 88.0000 | 73.0000 | 50.0000 | |

What is claimed is:

1. A method for improving cardiac output, comprising administering chemically-modified, stroma-free hemoglobin to a patient suffering from burn shock in an amount effective to increase cardiac output.

2. The method of claim 1, wherein said chemically-modified, stroma-free hemoglobin is delivered in a resuscitation fluid volume delivered in a cumulative dose of 100 to 2000 mg/kg of body weight during the course of a resuscitative regimen.

3. The method of claim 2, wherein half of said resuscitative fluid volume is administered during the first 8 hours post trauma, and the remaining half of said fluid volume is administered during the remainder of 24 hours post trauma.

4. The method of claim 1, wherein said chemically-modified, stroma-free hemoglobin is cross-linked or polymerized hemoglobin.

5. The method of claim 2, wherein the said resuscitative fluid volume is determined by a method selected from the group consisting of the Parkland formula, the Evans formula, and the Brooke formula.

6. A method for improving cardiac output, comprising administering diaspirin-crosslinked, stroma-free hemoglobin to a patient suffering from burn shock in an amount effective to increase cardiac output.

7. The method of claim 6, wherein said diaspirin-crosslinked, stroma-free hemoglobin is delivered in a resuscitation fluid volume in a cumulative dose of 100 to 2000 mg/kg of body weight during the course of a resuscitative regimen.

8. The method of claim 7, wherein half of said resuscitative fluid volume is administered during the first 8 hours post trauma, and the remaining half of said fluid volume is administered during the remainder of 24 hours post trauma.

9. The method of claim 7, herein the said resuscitative fluid volume is determined by a method selected from the group consisting of the Parkland formula, the Evans formula, and the Brooke formula.

* * * * *